(12) United States Patent
Ewenson et al.

(10) Patent No.: US 6,399,835 B1
(45) Date of Patent: Jun. 4, 2002

(54) PROCESS FOR ELECTROPHILIC AROMATIC SUBSTITUTION

(75) Inventors: Ariel Ewenson; David Itzhak; Miriam Freiberg Bergstein, all of Omer; Asher Shushan; Bertha Croitoru, both of Beer-Sheva; David Beneish, Omer; Naim Faza, Ramleh, all of (IL)

(73) Assignee: Bromine Compounds Ltd. (IL)

( * ) Notice: Subject to any disclaimer, the term of this patent is extended or adjusted under 35 U.S.C. 154(b) by 0 days.

(21) Appl. No.: 09/543,791

(22) Filed: Apr. 6, 2000

Related U.S. Application Data

(63) Continuation of application No. PCT/IL98/00489, filed on Oct. 8, 1998.

(30) Foreign Application Priority Data

Oct. 9, 1997 (IL) .................................................. 121933

(51) Int. Cl.⁷ ........................... C07C 45/61; C07C 17/02
(52) U.S. Cl. ....................... 568/490; 568/331; 568/491; 568/656; 570/143; 570/190; 585/462; 585/463
(58) Field of Search ................................ 568/331, 490, 568/491, 495, 656, 426, 433, 437, 628, 937; 570/127, 143, 190, 201; 585/446, 462, 463

(56) References Cited

U.S. PATENT DOCUMENTS 4,879,353 A * 11/1989 Sanders et al. ............. 525/357

FOREIGN PATENT DOCUMENTS

| EP | 0 262 919 | 4/1988 |
|---|---|---|
| GB | 1125077 | 8/1968 |
| GB | 1 235 240 | 6/1971 |
| GB | 1 344 965 | 1/1974 |
| JP | 62-48641 | 3/1987 |
| JP | 62-148465 | 7/1987 |
| JP | 4-356438 | 12/1992 |
| SU | 235040 | 11/1967 |

OTHER PUBLICATIONS

Chemical Abstracts, vol. 77, No. 5, 1972, Columbus, Ohio, USA, abstract No. 34140, A. M. Mitrokhin, "Alkylphenols," XP002089784, corresponding to SU 235040.

* cited by examiner

*Primary Examiner*—Sreeni Padmanabhan
(74) *Attorney, Agent, or Firm*—Lerner, David, Littenberg, Krumholz & Mentlik, LLP

(57) ABSTRACT

Processes for the electrophilic substitution of aromatic compounds, such as alkylation, with a desired substituent are disclosed. The processes include contacting the aromatic compound, a precursor of the desired substituent and an aqueous reagent containing zinc halide at elevated temperatures such as above 50° C.

33 Claims, 2 Drawing Sheets

US 6,399,835 B1

PROCESS FOR ELECTROPHILIC AROMATIC SUBSTITUTION

CROSS-REFERENCE TO RELATED APPLICATIONS

The present application is a continuation of International Application No. PCT/IL98/00489, filed on Oct. 8, 1998, the disclosure of which is incorporated by reference herein.

FIELD OF THE INVENTION

The present invention is in the field of organic synthesis, and is specifically related to a process for electrophilic substitution on aromatic compounds.

BACKGROUND OF THE INVENTION

The term electrophilic aromatic substitutions covers a broad class of reactions in which an electrophile is linked to an aromatic compound instead of a leaving group, which is generally a hydrogen atom. The electrophile may be a heteroatom, such as in the case of halogenation reactions. In acylation and alkylation reactions, a carbon side chain is introduced onto the aromatic ring.

The art teaches that the above mentioned reactions are catalyzed by certain Lewis acids. In the halogenation of some aromatic compounds, such as, for example, benzene, ferric halide or aluminum halide are typically employed as the catalytic reagent. In acylation and alkylation reactions (Friedel-Crafts and related processes), aluminum halide is accepted as the preferred catalyst. Other reagents known in the art for the catalysis of electrophilic aromatic substitutions are boron trifluoride or strong acids.

While aluminum chloride is considered to be a powerful catalyst for the purpose of electrophilic aromatic substitutions, a major drawback associated with its use is that it is not recyclable and cannot be employed in a subsequent reaction, since aluminum chloride undergoes hydrolysis, reacting violently with water to produce HCl. The production of wastes which are expensive to dispose of, leading to increases in the overall production costs, significantly impair the productivity of any industrial process employing said catalyst.

Another relevant synthetic problem is concerned with the orientation of electrophilic substitution on the aromatic ring. It is well known that if the substrate undergoing the reaction bears substituent groups, e.g. halogens, carbonyls or ether linkages, this will often strongly influence the pattern of a subsequent substitution, so that certain sites on the aromatic ring system will be preferred, and other sites will be disfavored. In many instances, however, it is desired to substitute at the disfavored positions, and therefore it would be useful to provide a means for substitution at these disfavored sites when necessary.

Four situations, which illustrate the foregoing drawbacks of the state of the art with respect to certain compounds of great industrial importance, are as follows:

1. 5-bromo-2-chloro-4-fluoroanisole (hereinafter 5-BCFA) is a compound useful as an intermediate in the synthesis of certain agrochemicals. The particular substitution pattern of 5-BCFA makes the synthesis of this compound (in preference to the corresponding 6-bromo compound) a challenge. Although means of preparing 5-BCFA via multi-step synthesis are conceivable, such processes, like many multi-step syntheses, would be expensive to carry out on a large scale and would therefore not readily lend themselves to industrial exploitation.

For industrial use, a desirable preparation of 5-BCFA would involve direct bromination of 2-chloro-4-fluoroanisole (hereinafter "CFA"). JP 4-356438 A2 discloses the direct bromination of CFA, using sulfuric acid as the reaction medium. However, this process is reported to yield 27% of the desired 5-bromo isomer, after column chromatography. This method is not readily amenable to large scale industrial production.

2. 6-acetyl-2-methoxy naphthalene (6-AMN) is an intermediate in the synthesis of naproxen, an anti-inflmatory agent. One method for the production of 6-AMN involves a three-step process starting from 2-methoxy napthalene (neroline), comprising protection of neroline at the 1-position, acylation at the 6-position using $AlCl_3$ as catalyst, and removal of the protecting group to yield 6-AMN. Such a process uses large amounts of $AlCl_3$ and generates large amounts of waste; therefore alternatives to this process which use less reagent, generate fewer wastes, and involve fewer steps would be be beneficial.

3. An intermediate in the production of 3-phenoxy benzaldehyde, a compound used for the production of pyrethroids, is 3-bromobenzaldehyde. Processes currently used for this bromination involve massive amounts of aluminum chloride, which generate large amounts of aluminous wastes and increase production costs. An inexpensive, recyclable $AlCl_3$ replacement would help lower costs and lessen the environmental impact.

4. 3-bromo-4fluorobenzaldehyde is a starting material for the synthesis of effective agrochemicals. It can be prepared by bromination of 4-fluorobenzaldehyde by using large amounts of aluminum chloride. This, again, involves the production of great masses of waste. As stated hereinbefore, recyclable alternatives to $AlCl_3$ would help lower costs and lessen the environmental impact of this process.

Other attempts reported in the art with reference to electrophilic aromatic substitutions are directed to the alkylation of phenols or alkyl-substituted derivatives thereof ie., to the alkylation of aromatic substrates which are considered highly activated, and therefore, are expected to undergo the substitution without special difficulty. GB 1235240 and GB 1344965 disclose processes for the alkylation of phenols or alkyl-substituted phenols, using catalytic system comprising zinc bromide or zinc chloride and hydrogen bromide or hydrogen chloride. SU 235040 discloses the alkylation of substituted phenol, using zinc chloride, HCl and alkaline salts, and specifically NaCl, which is alleged to increase the reaction yield by 10 to 15%, at a high temperature.

Otherwise, aqueous solutions of zinc bromide are generally known in the art as completion fluids for oil drilling.

JP 62-148465 describes the bromination of Bisphenol S in an organic solvent at a temperature in the range between 10 to 50° C., using hydrobromic acid solution, or a mixture of bromine and water, hydrogen peroxide and zinc halide. JP 62-48641 describes a corresponding process using Bisphenol A as the substrate.

It is an object of the invention to provide a simple and inexpensive process for electrophilic aromatic substitutions, in particular for halogenations, acylations and alkylations.

It is another object of the invention to provide such a process in which the principal reagent is of low toxicity and may be recycled, thereby reducing the amount of reagent required, reducing the amount of waste produced, and limiting the danger to man and the environment.

It is another purpose of the present invention to provide a process for electrophilic aromatic substitution in which the selectivity of the substitution towards a desired site on the aromatic ring system is improved with respect to presently known processes.

Other objects and advantages of the present invention will become apparent as the description proceeds.

SUMMARY OF THE INVENTION

The present invention provides a process for the electrophilic substitution of an aromatic compound, comprising contacting said aromatic compound, a precursor of the desired substituent and an aqueous reagent containing zinc halide, at an elevated temperature.

The preferred electrophilic aromatic substitution reactions according to the present invention are selected from among halogenation, acylation and alkylation reactions, provided that if the reaction is an alkylation, then the aqueous reagent contains zinc bromide, a bromide salt of an alkali metal or an alkaline earth metal, preferably LiBr, and an acid. By the term halogenation, particularly bromination and chlorination are intended.

It has been surprisingly found by the inventors, that an aqueous medium containing zinc halide, e.g., $ZnBr_2$ and $ZnCl_2$, which, as stated above, was previously known for use as completion fluids for oil drilling, may be applied as a recyclable reagent for a variety of electrophilic substitutions of aromatic compounds, at an elevated temperature, typically at a temperature above 50° C., and preferably between 60 to 160° C. Thus, an important feature of the present invention is the wide application of said aqueous reagent containing zinc halide as a primary medium for electrophilic aromatic substitutions, which can optionally be adapted with ease according to the requirements of the particular substitution intended. For example, when the electrophilic substitution is an alkylation reaction of aromatic compounds, the zinc halide present in said aqueous reagent is zinc bromide, together with an acid and a corresponding bromide salt of an alkali metal or an alkaline earth metal, which is preferably LiBr. The process according to the present invention is useful even for the substitution of strongly deactivated aromatic substrates, allowing convenient medium recycling without a significant decrease in the effectiveness of the catalytic medium, as well as improved conversion of the said aromatic substrate to the desired substituted derivative.

DETAILED DESCRIPTION OF PREFERRED EMBODIMENTS

Figure 1:
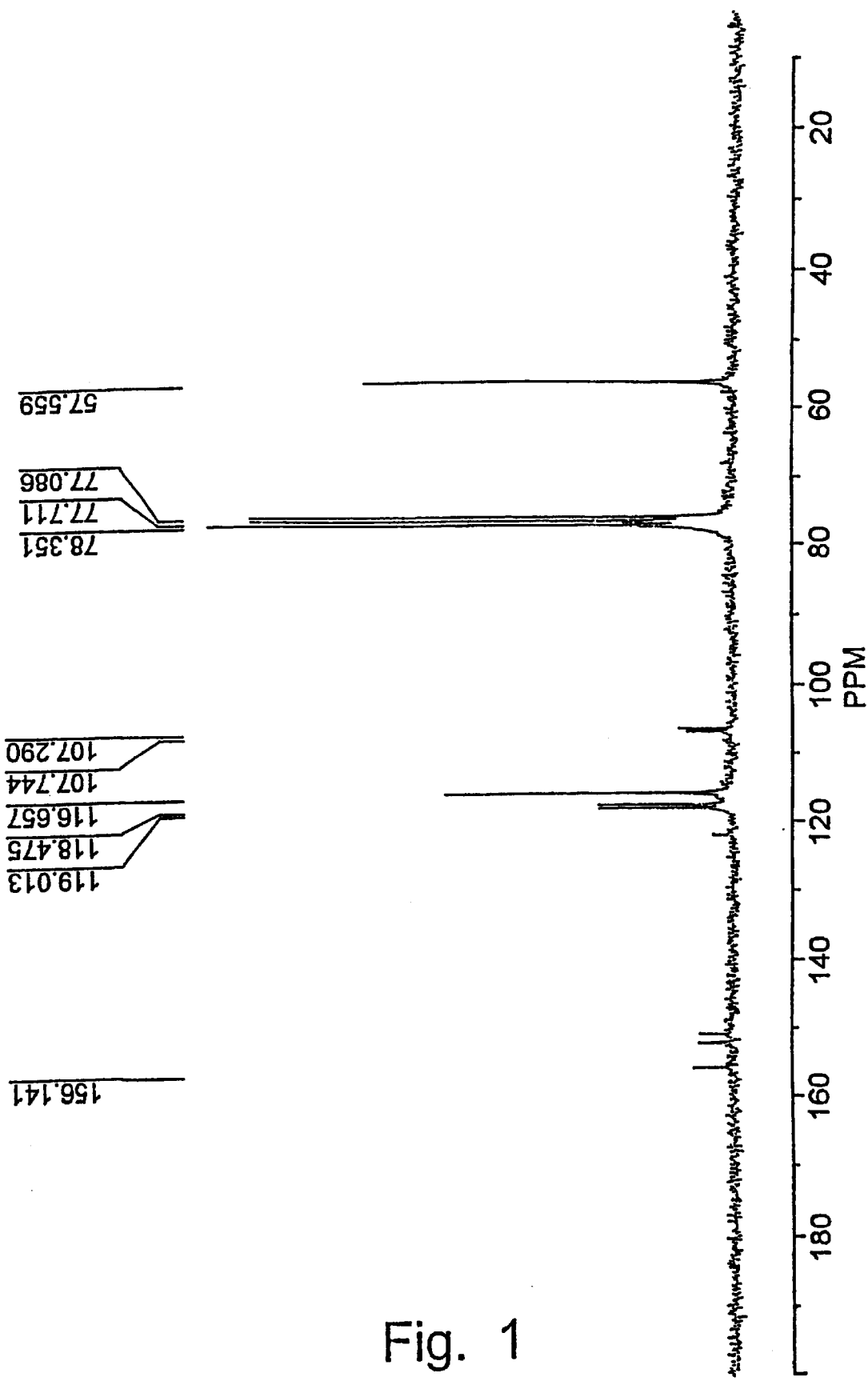
FIG. 1 is the $^{13}C$ NMR spectrum of 5-bromo-2-chloro-4-fluoroanisole.

The process for electrophilic substitution of an aromatic compound, comprises, according to the present invention, contacting said aromatic compound, a precursor of the desired substituent and an aqueous reagent containing zinc halide, at an elevated temperature.

According to a preferred embodiment of the process according to the present invention, pertinent for halogenation reactions, the aqueous reagent containing zinc halide is a concentrated aqueous solution of zinc halide, i.e., a brine, wherein the concentration of the zinc halide varies between 50 to 90, and preferably between 75 to 90 weight %.

According to another variant of the present invention, related to the aqueous reagent containing zinc halide employed in the halogenation reactions, it has been found that certain additives, and in particular, certain water soluble halide salts, and more specifically, the corresponding lithium halide salts, may enhance the effectiveness of the catalysis of the reaction and increase the conversion of the aromatic substrate to the desired substituted derivative. According to this variant, the aqueous reagent containing zinc halide, additionally comprises the corresponding lithium halide salt, wherein the molar ratio between said zinc halide and said lithium halide in said aqueous reagent varies between 4:1 to 1:1, said ratio preferably being about 1.4:1. Most preferably, the molar ratio between the water and the zinc halide in said aqueous reagent varies between 5:1 to 1:1, and is optimally about 1.7:1. The presence of this lithium salt additive has proven to be advantageous in particular for the halogenation of aromatic aldehydes, significantly reducing the occurrence of undesired side reactions, such as the oxidation of the aldehyde group.

Another aspect of the present invention, related to the aqueous reagent containing zinc halide employed in the halogenation reactions, is the surprising finding that a solution of zinc halide in water, in particular a brine containing between 70 to 90 weight % zinc halide, and more preferably, about 78 weight % zinc halide, can behave as an anhydrous medium, making it compatible with compounds such as aluminum halides, which, as explained hereinbefore, are known to react violently with water. According to this aspect of the present invention, a process for the halogenation of aromatic compound is provided, which comprises contacting said aromatic compound, a precursor of bromine atom or chlorine atom and an aqueous reagent containing zinc halide which is an aqueous solution in a concentration of between 70 to 90 weight % zinc halide, and preferably, about 78 weight % zinc halide, at an elevated temperature, wherein said solution additionally comprises the corresponding aluminum halide, e.g., $AlBr_3$ or $AlCl_3$. The aluminum halide may be formed in situ by addition of elemental aluminum to the reaction medium, preferably in the form of aluminum powder, together with the corresponding halogen, or it may be added separately as prepared $AlBr_3$ or $AlCl_3$. The molar ratio between the zinc halide and the aluminum halide in said aqueous solution may vary between 40:1 to 25:1, and is preferably around 32:1.

The preferred precursor of a halogen substituent according to the process of the present invention is molecular bromine, $Br_2$, or molecular chlorine, $Cl_2$.

According to the present invention, pertinent for acylations reactions, the aqueous reagent containing zinc halide is zinc halide brine wherein the concentration of said zinc halide is between 70 to 90 wt. %, more preferably about 78 wt. %. The precursor of the acyl group substituent is an acylating agent which is preferably selected from among carboxylic acid derivatives such as anhydrides or acyl halides, employed in an excess relative to the aromatic compound to allow a substantially complete neutralization of water from said aqueous reagent, via the reaction of the water with said excess of the acylating agent, producing the corresponding acid form of said acylating agent.

It has been found that when the acylation process according to the present invention produces a mixture of isomers, a subsequent heating of the reaction mixture to a second temperature and maintaining the same at said second temperature may lead to an isomerization, i.e., may result in a substantial increase in the selectivity of the reaction towards a certain isomer. The present invention thus provides a process for acylating an aromatic compound, comprising contacting said aromatic compound, an aqueous reagent containing zinc halide and an acylating agent in an excess relative to said aromatic compound, to allow a substantially complete neutralization of water from said aqueous reagent, at a first elevated temperature for a first period of time, and if a mixture of isomers is produced in which the undesired, kinetically stable isomer predominates, heating the reaction mixture to a second temperature, which is preferably 20 to 40° C. higher than said first temperature, and maintaining said reaction mixture at said second temperature for a second period of time, to improve the selectivity of the reaction towards the desired, thermodynamically stable isomer. Furthermore, and this is another important feature of the present invention, it has also been found by the inventors that if said first period of time is shorter than said second period of time, and optionally, if the reaction mixture is heated substantially directly from room temperature to said second temperature, it may also be possible to improve the conversion of the starting material, thereby increasing the final amounts of the desired isomer. This is an important advantage of the present invention, which provides a simple means for controlling the selectivity of the reaction, rendering the acceptable procedures for preventing the formation of undesired isomers, involving protecting the undesired sites of the aromatic ring, redundant. Typically, said second temperature is about 20 to 40° C. higher than the first temperature, said second temperature preferably varying in the range between 100 to 120° C.

A preferred aromatic compound to be acylated according to this embodiment is 2-methoxynaphthalene, yielding 6-acyl-2-methoxynaphthalene in preference to the corresponding 1-acyl-2-methoxynaphthalene isomer.

According to the present invention, the process for electrophilic substitution of an aromatic compound, wherein said substitution is alkylation, comprises contacting a precursor of the desired alkyl substituent, an aromatic compound and an aqueous reagent containing zinc bromide, an acid and a corresponding bromide salt of an alkali metal or an alkaline earth metal preferably LiBr, at an elevated temperature.

The preferred aqueous reagent employed in the alkylation reactions according to the present invention is provided by an aqueous solution comprising zinc bromide, an acid which is preferably selected from among the group consisting of HBr and $H_3PO_4$, and a bromide salt of an alkali metal or an alkaline earth metal which is preferably lithium salt, i.e., LiBr. It has been surprisingly found by the inventors that the combination of zinc bromide, lithium bromide and an acid is in particular beneficial for carrying out the alkylation reaction. It has also been found that the presence of lithium bromide, has a significant effect on the kinetics of the alkylation reaction.

Preferably, when alkylation is intended, the concentration of the zinc bromide in the aqueous solution varies between 70 to 90 wt %. Preferably, the molar ratio between the acid and the zinc bromide is in the range between 6:1 to 0.4:1, and preferably between 5:1 to 0.5:1, while the molar ratio between the bromide salt of an alkali metal or an alkaline earth metal, which is preferably a lithium salt, and the zinc bromide catalyst is in the range between 1:4 to 1:1., and preferably between 1:1.7 to 1:1.

According to the embodiment of the invention related to the alkylation reactions, the precursor of the alkyl group substituent is an alkylating agent which is preferably selected from among alkenes, alcohols and alkyl halides.

Preferred suitable temperatures for performing the halogenation substitutions are within the range of from approximately 20 to 160° C., especially a temperature of about 60 to 150° C. is preferred. Suitable temperatures for carrying out the acylation reactions are within the range of from approximately 25° C. to 150° C., especially a temperature of about 80 to 120° C. is preferred. A preferred range of temperatures at which the alkylation is conducted according to the present invention is 70 to 130° C. More preferably, the reaction is carried out from about 80 to 120° C. The selection of the exact temperature and the duration of the reaction will be adjusted by the skilled person according to the specific reactants and the progress of the reaction monitored by known means.

The aromatic compound which may be subjected to the electrophilic substitution according to the present invention is preferably selected from among the group consisting of benzene, naphthalene and anthracene, which may be optionally substituted by one or more groups selected from halo, i.e., fluoro, chloro, bromo and iodo, alkoxy, nitro, alkylcarbonyl, formyl, amido and the like. Preferred aromatic compounds to be substituted according to the present invention are selected from benzene, benzaldehyde, 4-fluorobenzaldehyde, nitrobenzene, 2-chloro-4-fluoroanisole and 2-methoxynaphthalene.

The aqueous reagent containing zinc halide and the precursor of the desired substituent may be introduced into the reaction vessel separately from the aromatic compound to be substituted, or all three components may be introduced at the same time. Batch and continuous modes of operation are both applicable.

In another aspect of the present invention, an aqueous reagent for effecting electrophilic substitutions in aromatic compound is provided, which comprises zinc halide, to be contacted with said aromatic compound and a precursor of the desired substituent under elevated temperature. This reagent is adapted with ease to a variety of electrophilic aromatic substitutions. Thus, when the substitution is an alkylation, said aqueous reagent is further characterized in that it comprises zinc bromide, an acid and a corresponding bromide salt of an alkali metal or an alkaline earth metal, which is preferably a lithium salt.

As mentioned hereinbefore, an important advantage of the present invention is associated with the fact that the reaction medium may be easily recycled by standard procedures, and used in a subsequent reaction. The inventors have also found that when lithium halide is present together with the zinc halide in said aqueous reagent, a portion of said lithium salt is transferred to the organic phase, and in order to maintain the catalytic performance of the recycled zinc halide aqueous reagent, this portion should be back-extracted and combined with the said recycled zinc halide aqueous reagent.

All the above and other characteristics and advantages of the invention will be better understood through the following illustrative and non-limitative description of preferred embodiments thereof

EXAMPLES

Abbreviations used Throught the Examples

| | |
|---|---|
| BA | Benzaldehyde |
| BCFA | Bromo-2-chloro-4-fluoroanisole |
| BFA | 2-Bromo-4-fluoroanisole |
| CFA | 2-Chloro-4-fluoroanisole |
| 4-FA | 4-Fluoroanisole |
| 4-FP | 4-Fluorophenol |

-continued

| | |
|---|---|
| GC | Gas Chromatography |
| GCMS | Gas Chromatography Mass Spectrometry |
| HPLC | High Performance Liquid Chromatography |
| MC | Methylene chloride |
| MeCN | Acetonitrile |
| mBBA | Meta-bromobenzaldehyde |
| NMR | Nuclear magnetic resonance |
| PEG | Poly ethylene glycol |
| TEA | Triethyl amine |
| TFA | Trifluoroacetic acid |

Example 1

Preparation of 5-Bromo-2-Chloro-4-Fluoroanisole
Substitution: Bromination
Aqueous Reagent: Aqueous Solution of $ZnBr_2$ The following steps A–B illustrate means of preparing 4-Fluoroanisole and 2-chloro-4-fluoroanisole, using techniques known in the art, followed by step C, for converting said 2-chloro-4-fluoroanisole-to the desired 5-bromo-2-chloro-4-fluoroanisole. In Section D, the preparation of 6-bromo-2-chloro-4-fluoroanisole is detailed, for the purpose of comparison.

A. Synthesis of 4-Fluoroanisole

The following materials were fed into a three necked reaction flask, provided with magnetic stirring, a reflux condenser and a gas sparging inlet tube: 4-FP (15.76 g, 125 mmole), water (75 g), PEG 600 (0.3 g) and NaOH (40%, 24 g, 240 mmole). The mixture was stirred at 85° C. and MeBr (117 g) was fed in during seven hours, GC followup at this point showed 0.70% of 4-FP and 97% pFA (both area %).

After cooling to room temperature, the upper phase was separated and weighed 16.6 g (GC: 0.34% 4-FP, 98.8% 4-FA).

B. Synthesis of 2-Chloro-4-fluoroanisole

In a magnetically stirred two liter reaction flask, provided with a thermometer, a reflux condenser topped by a $CaCl_2$ moisture trap followed by a water scrubber and an addition funnel, were placed 4-FA (252 g, 2 mole) and TEA (6 g, 0.06 mole). Sulfuryl chloride (300 g, 2.2 mole) was fed during the course of 3.5 hours, accompanied by the evolution of gas (HCl and $SO_2$) visible by bubbling in the scrubber. During this time the temperature rose from 25 to 37° C. Two hours after the end of the addition, with the temperature set at 37° C., HPLC analysis showed ~97% of CFA present. During the course of a further 3 hours, at 40° C., a total of 9.6 g of sulfuryl chloride were added (grand total: 309.6 g, 2.27 mole). After a total of 8 hours, HPLC showed ~99% of FCA.

To the cooled solution was gradually added water (100 ml) during 15 minutes and the temperature rose from 27 to 30° C. Phases were separated and to the organic layer was slowly added 10% aqueous sodium carbonate (100 ml). The mixture was stirred for 15 minutes and phases were separated. Two further water washes followed (100 ml each) and after phase separation the organic layer was received as an emulsion. After drying the product over $CaCl_2$ pellets, the filtered, clear liquid weighed 315 g (98.1% yield, 98.8% pure CFA by HPLC).

Analytical Methods for Steps A and B:
GC:
4-FA: Column—glass, 5 foot×10 inch inner diameter, SP 1000 packing with Supelcoport 100/120 mesh. Initial temperature: 60° C., hold 1 minute; temperature gradient: 10° C./min; final temperature: 250° C. Injector and FID detector temperature: 270° C. Retention times: 4-FP: 9 minutes, 4-FA: 17 minutes.

HPLC:
4-FA: Column—Zorbax SB Phenyl 150×4.5 mm column with matching precolumn cartridge; eluent gradient—MeCN (with 3% v/v Dimethoxy ethane) 30% (0')–45% (15')–90% (20')/ water (with 0.025% TFA, w/v); flow rate—1 ml/min.; detection –280 nm; peak times: 4-FP—4.3 min, 4-FA: 9.3 min.

2-Chloro-4-fluoro-anisole: Column—Econosil RP18 250×4.5 mm column; eluent (isocratic)—MeCN 70%/water 30%(with 0.025% TFA, w/v); flow rate—1 ml/min.; detection –280 nm; peak times: 4-FA—5.2–5.3 min, CFA: 6.3 min.

C. Synthesis of 5-Bromo-2-chloro-4-fluoroanisole

Into a 0.5 liter magnetically stirred reaction flask, provided with a thermometer, an addition funnel and a reflux condenser, were placed CFA (112 g, 0.7 mol) and $ZnBr_2$ (265.4 g, 0.92 mol, 78%, aq.). The mixture was warmed to 50° C. and bromine (112 g, 0.7 mol) was added over the course of two hours. After a further two hours at 54° C., HPLC analysis showed 3.4% CFA, 78.8% 5-BCFA, 12.9% 6-BCFA and assorted unknown impurities.

After cooling the mixture to 25° C., a light colored solid precipitated. This was separated from the mother liquor by filtration and it was then washed three times with 38% aqueous $NaHSO_3$ (50 ml each wash). At this point a KI paper test showed no oxidizing species present in the cake. The cake was then further washed three times with water (50 ml each wash) and it was then dried under vacuum at 50–60° C. for six hours. The isolated weight of the product was 80 g (99% pure 5-BCFA by HPLC, m.p.: 72.2–73.2° C., contains 18 ppm of Zn++ by atomic absorption spectrometry).

The mother liquor from the first filtration was collected separately from further washes: it consisted of two phases, both bromine-colored. After cooling overnight at 5° C. a second crop of product was collected by filtration: after washing as described above and drying under vacuum, the product weighed 9.5 g (98% pure 5-BCFA by HPLC). The total weight of isolated product was thus 89.5 g (53.4% yield).

The $ZnBr_2$ filtrate was separated from the remaining organic phase (40 g) and it was then extracted three times with MC (15 ml each extraction).

The separated, bromine-colored MC phase was combined with the above organic phase, decolorized with bisulfite and evaporated to a semisolid mass (49 g). After cooling this mixture overnight, a third crop of product was isolated (4.2 g, 94.7% pure 5-BCFA by HPLC). From this last mother liquor was isolated a further crop of solids (2.5 g, 74.7% 6-BCFA, 23% 5-BCFA) and a yellow residue (35 g, 35% 5-BCFA, 32% 6-BCFA and impurities).

D. Synthesis of 6-Bromo-2-chloro-4-fluoro Anisole (For Comparative Analytical Purposes)

(i) Preparation of 2-Bromo-4-anisole

4-FA (3.15 g, 25 mmol) and MC (10 ml) were charged into a magnetically stirred 50 ml flask, fitted with a condenser and a thermometer. Bromine (4 g, 25 mmol) was fed at room temperature during the course of 0.5 hours, with the aid of a syringe pump. The reaction was followed up by HPLC and more bromine (0.4 g) was added in 0.1 g portions after 3 hours of reaction. After 6.5 hours the reaction was stopped by the addition of a small amount of 38% aqueous sodium bisulfite. Phases were separated and the organic layer was washed with water. Evaporation of the solvent at the pump gave 5 g (~97% yield) of oily crude product which contained 97.3% 2-BFA and 2% starting material by qualitative HPLC.

(ii) Preparation of 6-BCFA

Into a 10 ml ReactiVial provided with a condenser and magnetic stirring were fed crude 2-BFA (2.56 g, 12.4 mmol) and two drops of TEA. Sulfuryl chloride (1.84 g, 13.6 mmol) was fed from a syringe pump in the course of 0.5 hours. The mixture was stirred for one hour at room temperature and at 50–60° C. for a further hour, while monitoring its progress by means of HPLC. Eventually, the temperature was stabilized at 40° C. for the last 6 hours. About 2.5 hours after the beginning, an excess of $SO_2Cl_2$ (9.1 g, 66.6 mmol) was added in differently sized portions, at approximately 1.5 hour intervals, together with small amounts of TEA. The reaction was discontinued after a total of 9 hours and the mixture was mixed with 10 ml of water, at which point the temperature rose fast to 60° C. Phases were separated and the organic layer was washed with 10% NaOH (10 ml), water (20 ml), 1% HCl (10 ml) followed by a large number of water washes until the pH of the washes was 5. Upon cooling the layer, white solids precipitated, which were collected by filtration and washed with water. HPLC showed that this solid was 92.5% 6-BCFA contaminated by ~7.5% 5-BCFA.

Analytical Methods for Steps C and D:

HPLC: 5-BCFA and 6-BCFA: Column—Econosil RP18 250×4.5 mm column; eluent (isocratic)—MeCN 70%/water 30%(with 0.025% TFA, w/v); flow rate—1 ml/min.; detection −280 nm; peak times: 5-BCFA—9.4–9.5 min, 6-BCFA—10.3–10.4 min.

$^1H$ NMR: The proton spectrum of the material identified as 5-BCFA shows the following absorptions (d=doublet, m=multiplet, s=singlet): 3.67 ppm, s, ~3H; 7.05 ppm (average), d (J=5.87 Hz), ~1H; 7.18 ppm (ave.), d (J=7.82 Hz), ~1 H; 7.25 ppm ($CDCl_3$).

The 6-Bromo isomer (contaminated by the 5-Br isomer) shows the following absorptions: 3.87 ppm (ave.), s, ~3H; 7.09 ppm (ave.), m, ~1H; 7.22 ppm, m (incl. $CDCl_3$), ~1H.

Figure 2:
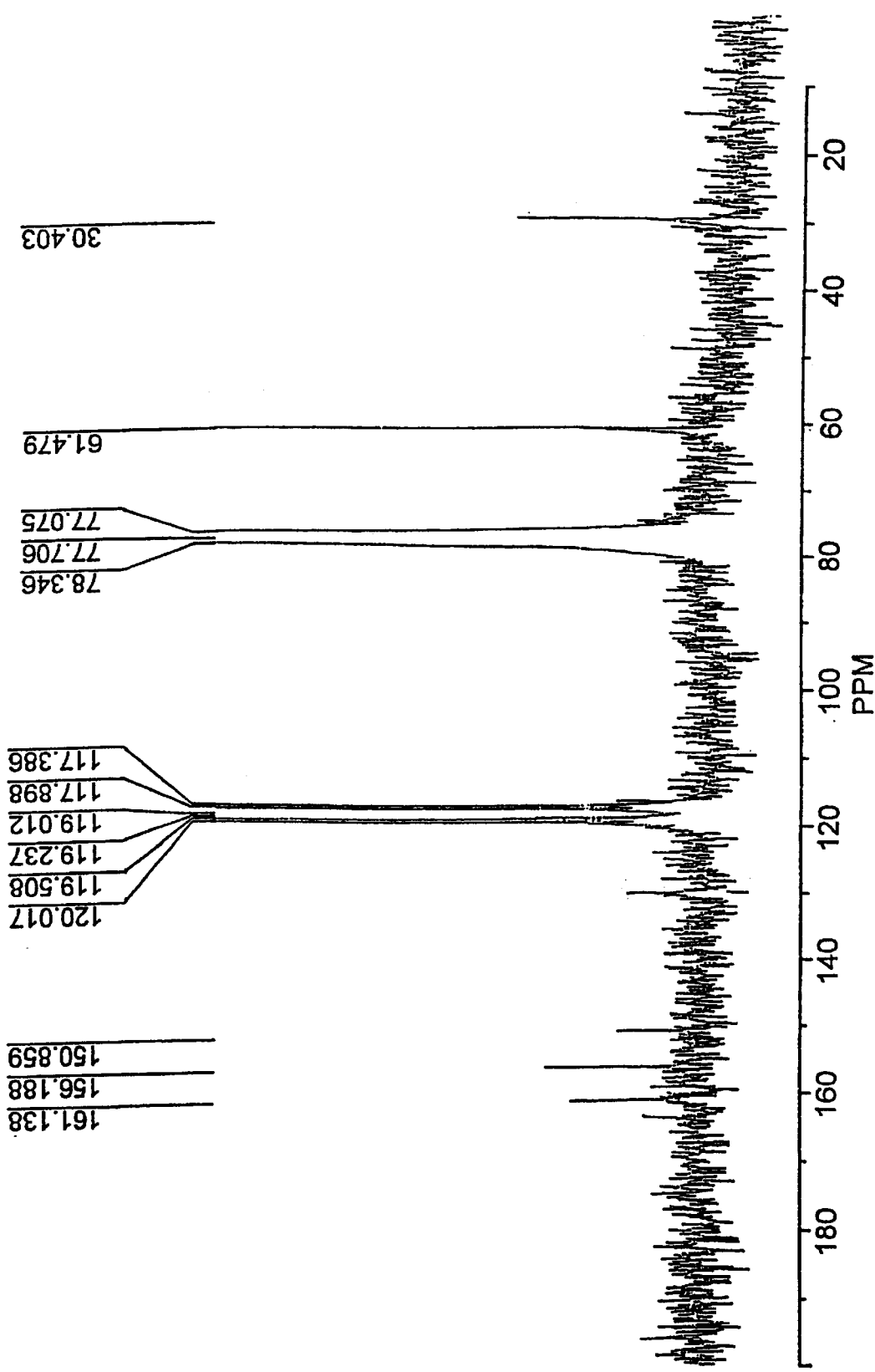
FIG. 2 is the $^{13}C$ NMR spectrum of 6-bromo-2-chloro-4-fluoroanisole.

$^{13}C$ NMR: FIGS. 1 and 2 show the $^{13}C$ NMR spectra of 5-BCFA and 6-BCFA, respectively.

Elemental analysis of 5-BCFA: (Performed at the Microanalytical Lab, Hebrew University of Jerusalem):

|  | C (%) | H (%) | Br (%) | Cl (%) | F (%) |
|---|---|---|---|---|---|
| Calculated | 35.1 | 2.1 | 33.4 | 14.8 | 7.9 |
| Experimental | 34.7 | 2.1 | 32.9 | 14.1 | 9.0 |

It is apparent from the above data that the process according to the present invention selectively yields the 5-Br isomer, i.e., 5-bromo-2-chloro-4-fluoroanisole.

Example 2

Preparation of 6-Acyl-2-methoxy Naphthalene
Substitution; Acylation
Aqueous Reagent: Aqueous Solution of $ZnBr_2$ Into a 100 ml reaction flask provided with a magnetic stirrer and a reflux condenser connected to a calcium chloride moisture exclusion trap were fed at room temperature aqueous zinc bromide 78 wt. % solution (5.1 g, 17.7 mmol), 2-methoxynaphthalene (1.41 g, 8.9 mmol) and acetic anhydride (7.34 g, 72 mmol). The mixture was warmed to 80–100° C. and was kept at said temperature for different periods. A further portion of acetic anhydride (1 g) was added and the mixture was heated to 120° C. HPLC analysis of the mixture showed the results shown in Table 1 below for two experiments.

TABLE 1

| Experiment | Time (Hours) | (° C.) | Neroline | 1-AMN | 6-AMN | others |
|---|---|---|---|---|---|---|
| 1 | 9 | 80 | 24 | 60 | 8 | 8 |
|  | 2 | 120 | 27 | 4 | 48 | 21 |
| 2 | 0.5 | 100 | 66 | 26 | 4 | 4 |
|  | 10.5 | 120 | 16 | 5 | 59 | 20 |

Example 3

Preparation of 3-Bromo Benzaldehyde

Substitution: Bromination

Aqueous Reagent: Aqueous Solution of $ZnBr_2$

Into a 250 ml glass autoclave (Buchi Glas Uster MiniClave) provided with magnetic stirring were charged aqueous zinc bromide (82%, 250 g), benzaldehyde (26.5 g, 250 mmol), and bromine (40 g, 250 mmol), under a blanket of nitrogen.

The vessel was sealed and heated until the inner temperature of the vessel reached 65–70° C. After four hours HPLC analysis of a sample withdrawn from the reaction mixture showed 17.9% of benzaldehyde, 70.8% of meta-bromobenzaldehyde and 11% of impurities. The unreacted bromine was removed by purging the mixture with nitrogen and the organic component was extracted with methylene chloride. The organic extract was washed with water and with dilute NaOH. After evaporation of the solvent, the residue weighed 31.7 g. Vacuum distillation of the crude mixture gave by HPLC analysis 6.4 g of >97% pure benzaldehyde and 18 g of ~98% pure meta-bromobenzaldehyde (~39% yield).

Example 4

Preparation of 3-Bromo Benzaldehyde in Recycled Aqueous Zinc Bromide

Substitution: Bromination

Aqueous Reagent: Recycled Aqueous Solution of $ZnBr_2$

The aqueous phase of the above run was washed with methylene chloride to remove residual organic compounds. A portion of this used brine (~70% $ZnBr_2$, 245 g) was reacted in a similar fashion to the above example, with benzaldehyde (26.5 g, 250 mmol) and bromine (250 mmol). The product consisted of 22.1% benzaldehyde, 67.6% 3-Bromo-benzaldehyde and 10% impurities. After performing the same type of work up as above, followed by fractional distillation, 17 g of ~98% (HPLC) pure 3-Bromo-benzaldehyde (~37% yield) were obtained.

A summary of the reactions detailed in examples 3 and 4, and additional subsequent reaction employing recycled aqueous zinc bromide, are summarised in Table 2.

TABLE 2

| Run | ZnBr$_2$ solution g | Benzaldehyde moles | Br$_2$ moles | Temp. °C. | Time hours | HPLC (area %) BA | mBBA | Impurities |
|---|---|---|---|---|---|---|---|---|
| 1 | 250 | 0.25 | 0.25 | 65 | 4 | 17.9 | 70.8 | 11 |
| 2 | 245 (from 1) | 0.25 | 0.25 | 70 | 4 | 22.1 | 67.6 | 10 |
| 3 | 200 (from 2) | 0.2 | 0.2 | 68 | 5 | 39.7 | 50.5 | 9.6 |

Example 5
Preparation of Aqueous Zinc Bromide Containing In Situ Prepared Aluminium Bromide Into a reaction flask provided with mechanical stirring and an efficient reflux condenser were fed aqueous zinc bromide (78%, 660 g, 2.28 mol) and aluminium powder (10 g, 250 mmol). The mixture was stirred and warmed to 800° C. and bromine (85 g, 530 mmol) was slowly fed while the mixture became frothy and gas evolved from the reaction set-up. External heating was removed and the temperature was maintained at about 75° C. by controlling the rate of bromine input. After all the bromine had been introduced, the red solution was stirred for one hour at 90° C., then for another hour at 115° C. While cooling to room temperature the solution was purged with nitrogen, after which it was stored in a stoppered glass vessel.

Example 6
Preparation of 3-Bromo-4-fluorobenzaldehyde in Aqueous Zinc Bromide Solution Containing In Situ Prepared Aluminum Bromide Substitution: Bromination
Aromatic Compound: 4-fluorobenaldehyde
Aqueous Reagent: Aqueous Solution of ZnBr$_2$+AlBr$_3$ Into a 70 ml Teflon lined autoclave (UniSeal, Haifa, Israel) were fed a portion (10 ml) of the aluminum/bromine containing brine of Example 5, anhydrous zinc bromide (2.9 g, 12.87 mmol, Merck), 4-fluorobenzaldehyde (1.27 g, 10 mmol), iodine crystals (3 mg, 0.01 mmol) and bromine (1.6 g, 10 mmol). The vessel was sealed and the mixture was heated and magnetically stirred for 4 hours at 100° C. A sample of the product was withdrawn and analyzed by GC showing 26.9% starting material, 1.5% 4-fluorobenzoic acid, 69.5% 3-bromo-4-fluorobenzaldehyde, and several impurities.

Example 7
Preparation of 3-Bromo-4-fluorobenzaldehyde with Zinc Bromide in Aqueous Hydrogen Bromide Substitution: Bromination
Aromatic Compound: 4-fluorobenaldehyde
Aqueous Reagent: ZnBr$_2$ in Aqueous Solution of HBr Into a 70 ml Teflon lined autoclave (UniSeal, Haifa, Israel) were fed 48% aqueous hydrogen bromide (12 g), anhydrous zinc bromide (26 g, 120 mmol, Merck), 4-fluorobenzaldehyde (1.27 g, 10 mmol), iodine crystals (26 mg, 0.1 mmol) and bromine (1.7 g, 11 mmol). The vessel was sealed and the mixture was heated and magnetically stirred for 4 hours at 100° C. A sample of the product was withdrawn and analyzed by GC showing 28.9% of starting material, 64.9% of 3-bromo-4-fluorobenzaldehyde and several impurities.

The reaction mixture was extracted with dichloroethane and the aqueous phase was used in Example 8.

Example 8
Preparation of 3-Bromo-4-fluorobenzaldehyde with Recycled Zinc Bromide in Aqueous Hydrogen Bromide Substitution: Bromination
Aromatic Compound: 4-fluorobenaldehyde
Aqueous Reagent: recycled solution of ZnBr$_2$+HBr Into a 70 ml Teflon lined autoclave (UniSeal, Haifa, Israel) were placed the untreated aqueous phase of Example 7 (36.5 g), 4-fluorobenzaldehyde (1.26 g, 10 mmol), iodine crystals (26 mg, 0.1 mmol) and bromine (1.7 g, 11 mmol). The vessel was sealed and the mixture was heated and magnetically stirred for 4 hours at 100° C. A sample of the product was withdrawn and analyzed by GC showing 45.8% of starting material, 47.2% of 3-bromo-4-fluorobenzaldehyde and several impurities.

Example 9
Preparation of 3-Bromo-4-fluorobenzaldehyde in Aqueous Zinc Bromide Containing Commercial Aluminum Bromide Substitution: bromination
Aromatic Compound: 4-fluorobenzaldehyde
Aqueous Reagent: Aqueous Solution of ZnBr$_2$+AlBr$_3$ Into a 70 ml Teflon lined autoclave (UniSeal, Haifa, Israel) were fed aqueous zinc bromide (78%, 10 g), anhydrous zinc bromide (2.79 g, 120 mmol), anhydrous aluminum bromide (1 g, 3.7 mmol Janssen), 4-fluorobenzaldehyde (1.27 g, 10 mmol), iodine crystals (3 mg, 0.1 mmol) and bromine (1.9 g, 11 mmol). The vessel was sealed and the mixture was heated and magnetically stirred for 4 hours at 100° C. A sample of the product was withdrawn and analyzed by GC showing 27.4% of starting material, 1.4% of 4-fluorobenzoic acid, 3.3% of 3-bromo-4-fluorobenzoic acid, 65.7% 3-bromo-4-fluorobenzaldehyde and several impurities.

Example 10 (Comparative)
Preparation of 3-Bromo-4-fluorobenzaldehyde in Aqueous Zinc Bromide Containing Alumina Substitution: bromination
Aromatic Compound: 4-fluorobenzaldehyde
Aqueous Reagent: aqueous solution of ZnBr$_2$+alumina Into a 70 ml Teflon lined autoclave (UniSeal, Haifa, Israel) were fed aqueous zinc bromide (78%, 10 g), anhydrous zinc bromide (2.8 g, 124 mmol), basic alumina (1 g, Merck, catalogue #1076), 4-fluorobenzaldehyde (1.3 g, 10 mmol), iodine crystals (3 mg, 0.1 mmol) and bromine (1.9 g, 11 mmol). The vessel was sealed and the mixture was heated and magnetically stirred for 4 hours at 100° C. A sample of the product was withdrawn and analyzed by GC showing 45.3% of starting material, 1.0% of 4-fluorobenzoic acid, 1.6% of 3-bromo-4-fluorobenzoic acid, 49.2% of 3-bromo-4-fluorobenzaldehyde and several impurities.

Example 11

Preparation of 3-Bromo-4-fluorobenzaldehyde in Aqueous Zinc Halide Containing Additives Substitution: bromination
Aromatic Compound: 4-fluorobenzaldehyde
Aqueous Reagent: aqueous solution of $ZnBr_2$+additives Table 3 summarizes both experimental conditions and results for several reactions for preparing 3-bromo-4-fluorobenzaldehyde by brominating 4-fluorobenzaldehyde, in which the reaction medium comprises aqueous solution of $ZnBr_2$ together with various alkaline salts as additives. The abbreviations used are as follows: 4FBA—4-fluorobenzaldehyde; 3B4FBA—3-bromo-4-fluorobenzaldehyde; 4FBAcid—4-fluorobenzoic acid; 3B4FBAcid: 3-bromo-4-fluorobenzoic acid.

reflux condenser were added zinc chloride (42.0 gr, 0.32 mole), lithium chloride (10.0 gr, 0.24 mole), water (10 gr, 0.55 mole) and benzaldehyde (5.3 gr, 0.05 mole). The mixture was stirred and heated to 80° C. Chlorine gas was then fed into the reaction setup at such a rate that the temperature was kept around 80° C. After three hours, a sample analyzed by HPLC showed benzaldehyde (13%), 3-chloro benzoic acid (2%), 3-Chloro benzaldehyde (69%) and dichloro benzaldehyde isomers (16%).

Example 14

Preparation of 3-Chloro Nitrobenzene

Substitution: chlorination
Aromatic Compound: nitrobenzene
Aqueous Reagent: recycled aqueous solution of $ZnCl_2$+LiCl Into a 100 ml three necked reaction flask provided with mechanical strring, thermometer, fritted gas inlet tube and

TABLE 3

| Zinc halide, mmol | Additive solution salt | conc. (wt. %) | mmol | 4FBA mmol | $Br_2$ mmol | Temp. (° C.) | Time (h) | Products distribution (GC, area %) 4FBA | 3B4FBA | 4FBAcid | 3B4FBacid |
|---|---|---|---|---|---|---|---|---|---|---|---|
| $ZnBr_2$, 115 | LiBr | 50.30 | 70 | 10 | 11 | 100 | 4 | 35 | 63.3 | 1.6 | |
| $ZnBr_2$, 115 | $CaBr_2$ | 52.20 | 31 | 10 | 11 | 100 | 4 | 52 | 40.2 | | |
| $ZnBr_2$, 115 | NaBr | 48.60 | 57 | 10 | 11 | 100 | 4 | 53.5 | 46.5 | | |
| $ZnBr_2$, 115 | KBr | 40.00 | 40 | 10 | 11 | 100 | 4 | 74.9 | 18.5 | 4.3 | 2.3 |
| $ZnCl_2$, 191 | LiBr | 32.80 | 45 | 10 | 11 | 100 | 4 | 41.5 | 56.7 | 1.8 | |
| none | LiBr | 50.20 | 45 | 10 | 11 | 100 | 4 | 83 | | | 17 |
| none | NaBr | 48.60 | 45 | 10 | 11 | 100 | 4 | 77 | | | 33 |

Example 12

Preparation of 3-Bromo Nitrobenzene

Substitution: bromination

Aromatic Compound: Nitrobenzene

Aqueous Reagent: Recycled Aqueous Solution of $ZnBr_2$+LiBr

Into a 250 ml three necked reaction flask provided with mechanical stirring, thermometer, addition funnel and reflux condenser were added zinc bromide (213.7 gr, 0.95 mole), lithium bromide (60.7 gr, 0.71 mole), water (29.7 gr, 1.65 mole) and nitrobenzene (24.6 gr, 0.2 mole). The mixture was stirred and heated to 140° C. Bromine (42 gr, 0.26 mole) was then added at such a rate that the temperature was kept around 140° C. After four hours, a sample analyzed by HPLC showed nitrobenzene (3.4%), 3-bromo nitrobenzene (90%) and dibromo nitrobenzene isomers (6.6%).

After extractive work up with methylene chloride, the solvent was evaporated under reduced pressure yielding 34.6 gr of crude product (79% yield). The brine solution was used without further treatment in a subsequent bromination run; HPLC analysis of the recycle run product showed nitrobenzene (3.8%), 3-bromo nitrobenzene (80.4%), dibromo nitrobenzene isomers (8.1%) and unknown products (7.7%).

Example 13

Preparation of 3-Chloro Benzaldehyde

Substitution: chlorination
Aromatic Compound: benzaldehyde
Aqueous Reagent: aqueous solution of $ZnCl_2$+LiCl Into a 100 ml three necked reaction flask provided with mechanical stirring, thermometer, fritted gas inlet tube and reflux condenser were added zinc chloride (42.0 gr, 0.32 mole), lithium chloride (10.0 gr, 0.24 mole), water (10 gr, 0.55 mole) and nitrobenzene (6.2 gr, 0.05 mole). The mixture was stirred and heated to 120° C. Chlorine gas was then fed into the reaction setup at such a rate that the temperature was kept around 120° C. After three hours, a sample analyzed by HPLC showed nitrobenzene (9%), 3-Chloro nitrobenzene (83%), dichloro nitrobenzene isomers (5%) and unknown impurities (3%).

After extraction of the organic compounds with methylene chloride, the organic layer was repeatedly back-extracted with water. The aqueous extracts were combined with the brine solution and the added amount of water was removed under reduced pressure. The brine solution could then be re-used for a further bromination run; HPLC analysis of the recycle run product showed nitrobenzene (10.2%), 3-chloro nitrobenzene (82%), dichloro nitrobenzene isomers (5.1%) and unknown products (2.7%).

Examples 15–27

Preparation of Alkyl Benzenes

Substitution: alkylation
Aromatic Compound: benzene
Aqueous Reagent: $ZnBr_2$/$ZnCl_2$+acid+LiBr/LiCl Alkylation with octene was performed in aqueous solutions containing different mixtures of zinc brines and proton acids. All reactions were performed in three necked flasks provided with external heating, mechanical stirring, a reflux condenser and a thermometer. The reaction mixtures consisted of two phases and aliquots of the organic phase were analyzed by gas chromatography. For the purpose of clarity, the benzene peak was not integrated. Structures were assigned by GCMS.

Table 4 summarizes both experimental conditions and results. The products were mixtures of mono-octyl benzene isomers designated as "alkylbenzenes" in table 4. The compounds designated X1, X3 were impurities. Compounds designated X2 were intermediates. The data in the columns referring to octene, X1, X2, alkylbenzenes and X3 are given in terms of GC, area %.

The runs were performed by feeding into the flask benzene (15.6 g; 0.2 mole), octane 4.49 g; 0.04 mole), ZnBr$_2$ (85.6 g, 0.38 mole), LiBr (24.3 g; 0.28 mole), HBr (48%,

TABLE 4

| Ex. | Benzene (eq.) | Octene (eq.) | ZnX$_2$ (eq.) | LiX (eq.) | Acid (eq.) | X | Temp. (° C.) | Time (hours) | Octene | X1 | X2 | Alkyl benzenes | X3 |
|---|---|---|---|---|---|---|---|---|---|---|---|---|---|
| 15 | 5 | 1 | 9.5 | 7 | 7.4* | Br | 86–95 | 8 | 0.2 | 0.2 | 11.4 | 85.5 | 2.7 |
| 16 | 1 | 1 | 9.5 | 7 | 7.4* | Br | 120–130 | 2 | 1.8 | 5 | 14.2 | 61.8 | 17.2 |
| 17 | 1 | 1 |  |  | 7.4* | Br | 90 | 2 | 21.1 | 43.3 | 29.1 | 4.2 | 2.3 |
| 18 | 5 | 1 | 9.5 | 7 | 37.4& | Br | 84 | 6 | 0.2 | 6 | 3 | 80.1 | 10.7 |
| 19 | 5 | 1 | 0.95 | 0.7 | 0.74* | Br | 77 | 4 | 93.4 | 1.5 | 3 | 0.3 | 1.8 |
| 20 | 5 | 1 | 13.3 | 7 | 8# | Br | 90–92 | 8 | 0.4 | 1.4 | 0.9 | 93.4 | 3.9 |
| 21 | 5 | 1 | 13.3 | 7 | 8# | Cl | 115–120 | 8 |  | 1.25 | 0.6 | 95.1 | 1.8 |
| 22 | 5 | 1 | 9.5 | 7 | 7.4* | Cl | 82 | 6 | 5.9 | 14.85 | 18.4 | 60.4 | 0.45 |
| 23 | 5 | 1 |  |  | 37.4& |  | 85 | 6 |  | 0.9 | 95 | 3.9 | 0.2 |
| 24 | 5 | 1 | 9.5 |  | 37.4& | Cl | 88 | 6 | 60.75 | 13.4 | 33.1 | 1.4 | 4.75 |
| 25 | 5 | 1 | 9.5 | 7 | 7.4@ | Cl | 82 | 6 | 16.1 | 14.5 | 66.9 | 0.6 | 1.9 |
| 26 | 5 | 1 |  |  | 7.4* | Br | 78 | 4 | 59 |  | 41 |  |  |
| 27 | 5 | 1 |  |  | 8# | Br | 80 | 4 | 1.5 | 0.35 | 98 | 0.25 |  |

Notes — Acid:
*HBr 48%
HBr 62%
@HCl 32%
&H$_3$PO$_4$ 85%

It is apparent from the comparison of examples 15 and 25, that the combination of zinc bromide, lithium bromide and an acid is superior to the corresponding chloride combination.

Examples 28 and 29

Preparation of Alkyl Benzenes
Substitution: Alkylation
Aromatic Compound: Benzene
Aqueous Reagent: ZnBr$_2$+acid+LiBr, ZnBr$_2$+acid The following examples, summarized in Table 5, illustrate the superiority of a catalytic system comprising zinc bromide, an acid and lithium bromide (example 28), over a catalytic system lacking the lithium salt (example 29) according to the process of the present invention 50.0 g; 0.296 mole), detergent (2 drops) and heating to 85–95° C. for 8 hours. After each reaction, phases were separated at room temperature. The aqueous phase was used in subsequent alkylation runs without any further treatment or topping up.

TABLE 6

| Reaction (#) | Aqueous phase (from) | Octene | X1 | X2 | GC (%, Area) Alkyl benzenes | X3 |
|---|---|---|---|---|---|---|
| 1 | new | 0.6 | 6 | 5 | 83.7 | 4.6 |
| 2 | 1 | 1.6 | 8.8 | 5.4 | 78 | 6.5 |
| 3 | 2 | 2.1 | 1.7 | 25 | 70 | 1.2 |

TABLE 5

| Ex. | Benzene (eq.) | Octene (eq.) | ZnBr$_2$ (eq.) | LiBr (eq.) | HBr (48%) (eq.) | Temp. (° C.) | Time (hours) | Octene | X1 | X2 | Alkyl benzenes | X3 |
|---|---|---|---|---|---|---|---|---|---|---|---|---|
| 28 | 5 | 1 | 9.5 | 7 | 7.4 | 80–85 | 8 | 0.2 | — | 11.4 | 85.5 | 2.7 |
| 29 | 5 | 1 | 9.5 | 0 | 7.4 | 80–85 | 12 | 0.6 | — | 11.9 | 85 | 1.7 |

The surprising kinetic effect attributed to the presence of the lithium salt is clearly apparent from the above comparison, demonstrating that the duration of a reaction employing this additive is significantly shorter than a corresponding reaction lacking said lithium salt.

Example 30

Preparation of Alkyl Benzenes
Substitution: alkylation
Aromatic Compound: benzene
Aqueous Reagent: recycled ZnBr$_2$+acid+LiBr All reactions were performed in three necked flasks provided with external heating, mechanical stirring, a reflux condenser and a thermometer. The reaction mixtures consisted of two phases and aliquots of the organic phase were analyzed by gas chromatography.

It is evident from the above example that the aqueous reagent according to the present invention can be recycled and used in a subsequent reaction.

What is claimed is:
1. A process for electrophilic substitution of an aromatic compound wit a substituent, comprising contacting said aromatic compound, a precursor of said substituent and an aqueous reagent containing zinc halide, provided that when said electrophilic substitution comprises alkylation, said aqueous reagent further comprises a bromide salt of an alkali metal or an alkaline earth metal and an acid, and said zinc halide comprising zinc bromide, having a concentration of about 50% to 90% by weight.
2. A process according to claim 1 wherein said elevated temperature is above 50° C.
3. A process according to claim 1, wherein said electrophilic substitution comprises bromination or chlorination, said aqueous reagent comprising an aqueous solution of zinc bromide or zinc chloride.

4. A process according to claim 3, wherein said aqueous solution of zinc halide further comprises the corresponding lithium halide salt.

5. A process according to claim 4, wherein the molar ratio between said zinc halide and said lithium halide salts present in said aqueous solution varies between about 4:1 to 1:1, and the molar ratio between the water and said zinc halide in said aqueous solution varies between about 5:1 to 1:1.

6. A process according to claim 5, where the molar ratio between said zinc halide and said lithium halide is about 1.4:1, and the molar ratio between the water and said zinc halide is about 1.7:1.

7. A process according to claim 3, wherein said substituent comprises a precursor of bromine atom or chlorine atom, and wherein said aqueous reagent containing zinc halide comprises an aqueous solution in a concentration of between about 70 to 90 weight % zinc halide, said solution additionally comprising the aluminum halide.

8. A process according to claim 7, wherein said concentration of zinc halide in said aqueous solution is about 78 weight %, and the molar ratio between said zinc halide and said aluminum halide in said aqueous solution varies between about 40:1 and 25:1.

9. A process according to claim 1, wherein the electrophilic substitution comprises an alkylation reaction, said substituent comprises an alkyl group substituent comprising an alkylating agent selected from the group consisting of carboxylic acid derivatives which are anhydrides or all halides, said alkylating agent being present in an excess relative to said aromatic compound to allow a neutralization of water from said aqueous reagent.

10. A process according to claim 9, wherein said contacting is carried out at a first temperature above 50° C. for a first period of time.

11. A process according to claim 10, wherein a mixture of isomers is produced in which a kinetically stable isomer predominates, said process comprising heating said reaction mixture to a second temperature above 70° C. and maintaining said reaction mixture at said second temperature for a second period of time whereby the selectivity of said reaction towards said thermodynamically stable isomer is greater.

12. A process according to claim 11, wherein said first period of time is lesser than said second period of time.

13. A process according to claim 11, wherein said first period of time is negligible with respect to said second period of time.

14. A process according to claim 10, wherein said aromatic compound comprises 2-methoxynaphthalene, whereby the substituted derivative thereof comprises 6-acyl-2-methoxynaphthalene.

15. A process according to claim 1 wherein said bromide salt of an alkali metal or an alkaline earth metal comprises LiBr.

16. A process according to claim 15, wherein said acid is selected from the group consisting of HBr and $H_3PO_4$.

17. A process according to claim 16, wherein the concentration of said zinc bromide in said aqueous reagent is between about 70 to 90 weight %, the molar ratio between said acid and said zinc bromide is in the range between about 6:1 to 0.4:1 and the molar ratio between said lithium salt and said zinc bromide is in the range between about 1:4 to 1:1.

18. A process according to claim 1, wherein said electrophilic substitution comprises a halogenation reaction, and said elevated temperature is between about 60 to 150° C.

19. A process according to claim 1, wherein said electrophilic substitution comprises an acylation reaction, and said elevated temperature is between about 80 to 120° C.

20. A process according to claim 1, wherein said electrophilic substitution comprises an alkylation reaction, and said elevated temperature is between about 80 to 120° C.

21. A process according to claim 1, wherein said aromatic compound is selected from the group consisting of benzene, naphthalene and anthracene.

22. A process according to claim 21, wherein said benzene, naphthalene and anthracene are substituted by one or more components selected from the group consisting of halo, alkoxy, nitro, alkylcarbonyl, formyl and amido.

23. A process according to claim 22, wherein said halo component is selected from the group consisting of fluoro, chloro, bromo and iodo.

24. A process according to claim 23, wherein said aromatic compound is selected from the group consisting of benzene, benzaldehyde, 4-fluorobenzaldehyde, nitrobenzene, 2-chloro-4-fluoroanisole and 2-methoxynaphthalene.

25. A process according to claim 1 comprising recycling said aqueous reagent containing zinc halide for use in a subsequent electrophilic aromatic substitution.

26. The process of electrophilic substitution of claim 1, wherein the aqueous reagent comprises zinc halide.

27. The process of claim 26 comprising zinc halide for use in the process of electrolytic substitution.

28. The process according to claim 26 for halogenation or acylation, further comprising lithium halide.

29. The process according to claim 26 for alkylation, wherein said bromide salt of an alkaline metal or an alkaline earth metal comprises LiBr.

30. The process according to claim 26, wherein the aqueous reagent behaves as an anhydrous medium, comprising aluminum halide.

31. A process according to claim 11, wherein said second temperature is about 20° C. to 40° C. greater than said first temperature.

32. A process according to claim 11, wherein said second temperate is about 100° C. to 120° C.

33. A process for electrophilic substitution, excluding alkylation, of an aromatic compound with a substituent, comprising contacting said aromatic compound, a precursor of said substituent, and an aqueous reagent containing zinc halide comprising zinc bromide, having a concentration of about 50% to 90% by weight at an elevated temperature.

* * * * *

UNITED STATES PATENT AND TRADEMARK OFFICE
CERTIFICATE OF CORRECTION

PATENT NO. : 6,399,835 B1
DATED : June 4, 2002
INVENTOR(S) : Ariel Ewenson, David Itzhak, Miriam Freiberg Bergstein, Asher Shushan, Bertha Croitoru, David Beneish and Naim Faza It is certified that error appears in the above-identified patent and that said Letters Patent is hereby corrected as shown below:

Column 1,
Line 42, delete "impair" and insert -- impairs --.

Column 2,
Line 19, second occurrence, delete "be".

Column 3,
Line 33, delete ",".

Column 5,
Line 13, delete "shorther" and insert -- shorter --.

Column 6,
Line 59, delete "Throught" and insert -- throughout --.

Column 11,
Line 21, delete "800°" and insert -- 80° --.

Column 15,
Line 41, insert -- . --.

Column 16,
Line 56, delete "wit" and insert -- with --.

Column 17,
Line 41, delete "lesser" and insert -- less --.

Column 18,
Line 39, delete "alkaline" and insert -- alkali --.

Signed and Sealed this

Fifth Day of November, 2002

*Attest:*

JAMES E. ROGAN
*Attesting Officer*     *Director of the United States Patent and Trademark Office*